US009675279B2

(12) United States Patent
Henning

(10) Patent No.: US 9,675,279 B2
(45) Date of Patent: Jun. 13, 2017

(54) METHOD FOR DETERMINING THE TIME POINT OF A HEART MOVEMENT AND CORRESPONDING APPARATUS

(71) Applicant: SIEMENS AKTIENGESELLSCHAFT, Munich (DE)

(72) Inventor: Andre Henning, Erlangen (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 0 days.

(21) Appl. No.: 14/659,745

(22) Filed: Mar. 17, 2015

(65) Prior Publication Data
US 2015/0272479 A1    Oct. 1, 2015

(30) Foreign Application Priority Data
Mar. 28, 2014    (DE) .................. 10 2014 205 828

(51) Int. Cl.
*A61B 5/04*    (2006.01)
*A61N 1/00*    (2006.01)
(Continued)

(52) U.S. Cl.
CPC .......... *A61B 5/1102* (2013.01); *A61B 5/0402* (2013.01); *A61B 5/0456* (2013.01);
(Continued)

(58) Field of Classification Search
USPC ............................................ 600/513; 607/28
See application file for complete search history.

(56) References Cited

U.S. PATENT DOCUMENTS

| 7,389,136 B2 | 6/2008 | Avinash |
| 2003/0036693 A1 | 2/2003 | Bulkes |

(Continued)

FOREIGN PATENT DOCUMENTS

| CN | 1504164 A | 6/2004 |
| CN | 102805639 A | 12/2012 |

(Continued)

OTHER PUBLICATIONS

German Office Action Oct. 10, 2014.
Chinese Office Action and English translation thereof dated Feb. 27, 2017.

*Primary Examiner* — Nicole F Johnson
(74) *Attorney, Agent, or Firm* — Harness, Dickey & Pierce, P.L.C.

(57) ABSTRACT

A method for determining a time point of a heart movement is described, wherein an EKG signal showing the heart movement is received. A first time point is determined, after which a mechanical signal characterizing the heart movement will probably be received, as a function of the received EKG signal. A mechanical signal is also received after the determined first time point. The time point of a heart movement can be concluded based on the receive time point of the mechanical signal. An apparatus for determining a time point of a heart movement is also described. The apparatus has a first receive facility, a timing facility, a second receive facility, and an evaluation facility. The evaluation facility is configured to determine the receive time point of the mechanical signal and to determine a time point of a heart movement based on the determined receive time point of the mechanical signal.

17 Claims, 6 Drawing Sheets

(51) Int. Cl.
*A61B 5/11* (2006.01)
*A61B 5/0402* (2006.01)
*A61B 6/00* (2006.01)
*A61B 5/0456* (2006.01)
*A61B 6/03* (2006.01)
*A61B 5/021* (2006.01)
*A61B 5/00* (2006.01)
*A61B 5/055* (2006.01)

(52) U.S. Cl.
CPC .......... *A61B 5/7207* (2013.01); *A61B 5/7278* (2013.01); *A61B 5/7292* (2013.01); *A61B 6/032* (2013.01); *A61B 6/503* (2013.01); *A61B 6/541* (2013.01); *A61B 5/021* (2013.01); *A61B 5/055* (2013.01); *A61B 5/7225* (2013.01)

(56) References Cited

U.S. PATENT DOCUMENTS

| | | |
|---|---|---|
| 2004/0111038 A1 | 6/2004 | Salla et al. |
| 2008/0269825 A1* | 10/2008 | Chinchoy ............ A61N 1/3627 607/28 |
| 2011/0075906 A1 | 3/2011 | Allmendinger et al. |
| 2012/0253142 A1* | 10/2012 | Meger .................. A61B 5/1116 600/301 |
| 2012/0302900 A1* | 11/2012 | Yin ...................... A61B 5/0205 600/484 |
| 2012/0307964 A1 | 12/2012 | Hall |
| 2012/0310053 A1 | 12/2012 | Popescu |
| 2012/0310079 A1 | 12/2012 | Henning |
| 2013/0131530 A1 | 5/2013 | Brockway |
| 2015/0002331 A1 | 1/2015 | Allmendinger et al. |

FOREIGN PATENT DOCUMENTS

| | | |
|---|---|---|
| DE | 102009043633 A1 | 3/2011 |
| DE | 202012001096 U1 | 3/2012 |
| DE | 102010041777 A1 | 4/2012 |
| DE | 1020011076882 A1 | 12/2012 |
| DE | 102013212819 A1 | 1/2015 |

\* cited by examiner

METHOD FOR DETERMINING THE TIME POINT OF A HEART MOVEMENT AND CORRESPONDING APPARATUS

PRIORITY STATEMENT

The present application hereby claims priority under 35 U.S.C. §119 to German patent application number DE 102014205828.7 filed Mar. 28, 2014, the entire contents of which are hereby incorporated herein by reference.

FIELD

At least one embodiment of the invention relates to a method for determining the time point of a heart movement. The invention also relates to an apparatus for determining a time point of a heart movement. The invention further relates to a method for triggering an imaging system. Finally the invention relates to an imaging system.

BACKGROUND

During medical imaging of the heart recordings have to be taken of a moving object, the beating heart. If the movement is not taken into account, the images are blurred. This problem occurs for example with imaging systems using computed tomography, magnetic resonance tomography, positron emission tomography and with ultrasound systems. With CT recordings in particular it is disadvantageous for recordings to have to be repeated, as the patient is then exposed to a higher radiation dose.

It is the convention to attempt to synchronize or trigger recordings of the heart in a prospective manner using the heart's electrical signal, in other words generally by means of an electrocardiogram (EKG). To this end electrodes are positioned on the skin of the patient and one or more derivations of the EKG are segmented for characteristic features, generally the so-called R-wave. The derivations are voltage measurements between two points of the body. The R-wave (see also FIG. 4) is the most characteristic feature of an EKG. It is the first positive deflection of the QRS complex. The QRS complex correlates with ventricular excitation or the depolarization of the two ventricles.

The actual scan or image recording then takes place in a defined interval relative to the position of the R-wave, so that the influence of the inherent movement of the beating heart can be reduced. The reliability of synchronization or triggering, in other words both the sensitivity and the predicativity, or the amount of information provided by the signal and its temporal constancy, in other words for example the deviation of the relative positions of the measured signals from the true R-wave, are decisive for the quality of the imaging here. A corresponding method is described in DE 10 2010 041 777 A1.

It is however disadvantageous that the electrical excitation of the heart does not correlate fully with the relevant variable, the mechanical excitation of the heart. There is a patient-specific offset between the R-wave and the ejection of the atria of the heart, which is also subject to dynamic fluctuations due to mechanical influences such as respiration or patient movement and autoregulatory processes.

There are also alternative approaches, for example the use of the pulse wave at the finger (PPG=photoplethysmography). However this has a time offset, which only allows triggering retrospectively and not in real time. The technology cannot therefore be used in particular with computed tomography due to the particularities cited above.

Alternatively it is also possible to use capacitive sensors, a ballistocardiogram, radar or phonocardiography, which allow the mechanical excitation of the heart to be shown to some extent. However the recorded signals generally do not have unique maxima but rather a distribution to different maxima. With a real-time recording it is initially unclear which of the maxima corresponds to the heart movement to be detected. It is therefore not easy to determine the movement time point of the heart reliably in real time and respond for example to an arrhythmia in the signal.

The maxima of the graphs showing the mechanical excitation of the heart are frequently not very marked so they can barely be distinguished from one another. Also the maxima often follow one another very closely in said graphs so their resolution may be very problematic. The comparison of the maxima with reference curves, for example as part of a filter procedure (matched filter), also encounters major problems, as the shape of the curves is only fully known as it were in retrospect but the movement of the heart has to be determined in a prospective manner in order to terminate imaging accordingly.

The direct measurement of a physical variable characterizing the mechanical excitation of the heart therefore also gives rise to the problem of being able to guarantee a reliable prediction of heart movement in real time. In this instance it is also difficult to respond to particularities such as extrasystoles, which are generally associated with a change in the muscle contraction pattern and can therefore be reflected very differently in the biosignals. However as the heart moves in such an instance, such events also have to be registered reliably.

SUMMARY

At least one embodiment of the present invention is directed to a method, which allows a more precise and more reliable synchronization of imaging methods with the movement of the heart.

At least one embodiment of the present invention is directed to a method and at least one embodiment of the present invention is directed to an apparatus.

At least one embodiment of the inventive apparatus for determining a time point of a heart movement has a first receive facility, which is set up to receive an EKG signal showing a heart movement. The inventive apparatus also has a timing facility, which is set up to determine a first time point, after which a mechanical signal showing the heart movement will probably be received, as a function of the received EKG signal. The apparatus also has a second receive facility, which is set up to receive a mechanical signal after the determined first time point. At least one embodiment of the inventive apparatus also has an evaluation facility. The evaluation facility is set up to determine the receive time point of the mechanical signal and to determine a time point of a heart movement based on the determined receive time point of the mechanical signal.

It should be noted here that the first and second receive facility for receiving the EKG signal and the mechanical signal can also be embodied as a single receive facility, which can receive both signals from EKG sensors and signals from sensors for mechanical signals.

With at least one embodiment of the inventive method for triggering an imaging system, the initiating or triggering of an imaging system is performed as a function of the determined time point of the heart movement. By determining the time of image recording by the imaging system as a function of the initiation signal or trigger signal it is possible, if a particularly high image quality is required for the recording for example, to prevent image recording being performed during the heart movement and being adversely affected by it.

At least one embodiment of the inventive imaging system has at least one embodiment of the inventive apparatus for determining a time point of a heart movement.

At least one embodiment of the inventive computer program, which can be loaded directly into a storage unit of an inventive apparatus, has program code segments in order to execute all the steps of the cited method when the program is executed in the apparatus.

Further, particularly advantageous embodiments and developments of the invention will emerge from the dependent claims and the description which follows, it being possible for the independent claims of one claim category also to be developed in the same way as the dependent claims of a different claim category.

BRIEF DESCRIPTION OF THE DRAWINGS

Embodiments of the invention are described yet again in more detail in the following with reference to the accompanying figures based on example embodiments. The same components are shown with identical reference characters in the different figures. In the figures, which are generally not to scale.

DETAILED DESCRIPTION OF THE EXAMPLE EMBODIMENTS

Figure 1:
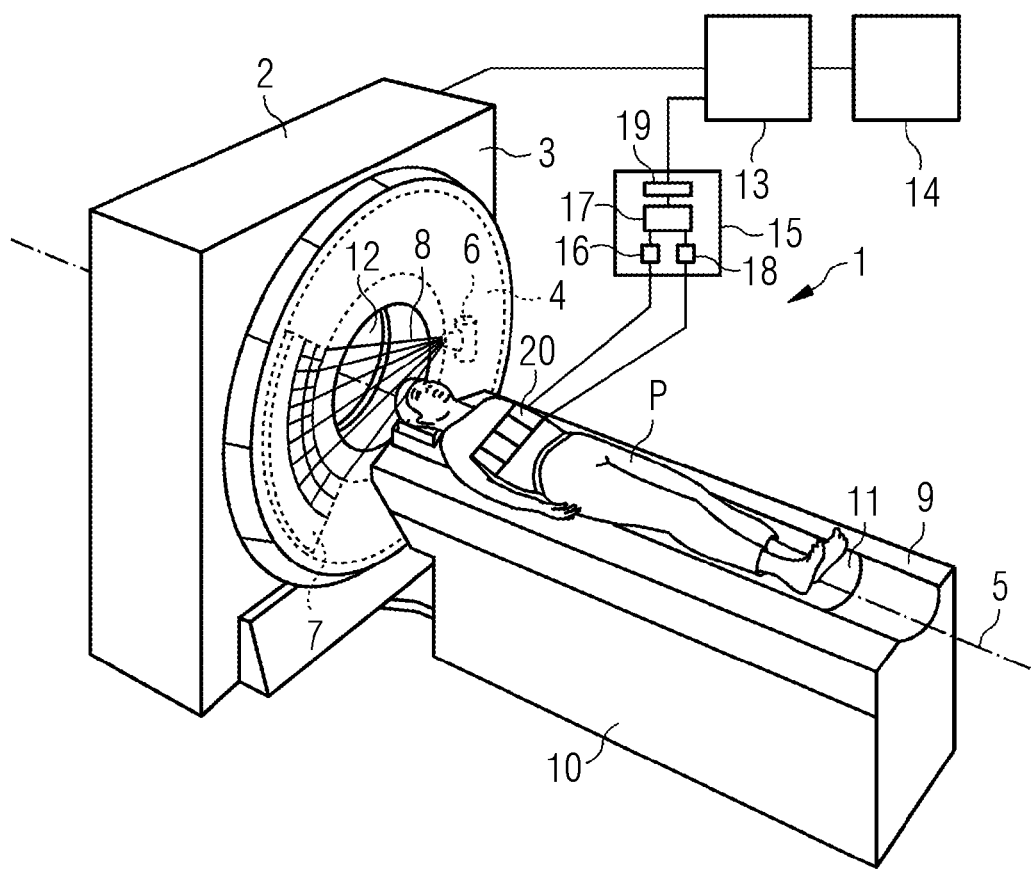
FIG. 1 shows a schematic diagram of an example embodiment of an inventive imaging system.

The present invention will be further described in detail in conjunction with the accompanying drawings and embodiments. It should be understood that the particular embodiments described herein are only used to illustrate the present invention but not to limit the present invention.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

Specific structural and functional details disclosed herein are merely representative for purposes of describing example embodiments of the present invention. This invention may, however, be embodied in many alternate forms and should not be construed as limited to only the embodiments set forth herein.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

According to at least one embodiment of the invention, an EKG signal showing a heart movement is first received. A first time point, after which a mechanical signal showing the heart movement will probably be received, is also determined as a function of the received EKG signal. The mechanical signal is then received after the determined first time point. The receive time point of the mechanical signal is determined and used to determine the time point of a heart movement.

In contrast to conventional methods therefore an individual signal showing heart movement, also conventionally referred to as a biosignal, is not used for triggering but rather a specific combination of electrical and mechanical information. The unique measurable electrical signal is used here to determine a time point for the expected mechanical signal, after which the mechanical signal will probably be received. Only when the mechanical signal has been received is a signal characterizing the heart movement output as a trigger pulse. Use of the information from the EKG therefore allows correct triggering, in particular when arrhythmias occur. The image recording of the imaging system can be clocked accordingly based on the trigger signal, so that the recordings are not adversely affected by the heart movement. For example activation of the image recording system is configured so that image recording does not take place during the heart movement but only during the relative rest state between heart movements.

At least one embodiment of the inventive apparatus for determining a time point of a heart movement has a first receive facility, which is set up to receive an EKG signal showing a heart movement. The inventive apparatus also has a timing facility, which is set up to determine a first time point, after which a mechanical signal showing the heart movement will probably be received, as a function of the received EKG signal. The apparatus also has a second receive facility, which is set up to receive a mechanical signal after the determined first time point. At least one embodiment of the inventive apparatus also has an evaluation facility. The evaluation facility is set up to determine the receive time point of the mechanical signal and to determine a time point of a heart movement based on the determined receive time point of the mechanical signal.

It should be noted here that the first and second receive facility for receiving the EKG signal and the mechanical signal can also be embodied as a single receive facility, which can receive both signals from EKG sensors and signals from sensors for mechanical signals.

With at least one embodiment of the inventive method for triggering an imaging system, the initiating or triggering of an imaging system is performed as a function of the determined time point of the heart movement. By determining the time of image recording by the imaging system as a function of the initiation signal or trigger signal it is possible, if a particularly high image quality is required for the recording for example, to prevent image recording being performed during the heart movement and being adversely affected by it.

At least one embodiment of the inventive imaging system has at least one embodiment of the inventive apparatus for determining a time point of a heart movement.

At least one embodiment of the inventive computer program, which can be loaded directly into a storage unit of an inventive apparatus, has program code segments in order to execute all the steps of the cited method when the program is executed in the apparatus.

Further, particularly advantageous embodiments and developments of the invention will emerge from the dependent claims and the description which follows, it being possible for the independent claims of one claim category also to be developed in the same way as the dependent claims of a different claim category.

In one embodiment of the inventive method, instead of a first time point a time interval, in which a mechanical signal showing the heart movement will probably be received, is determined as a function of the received EKG signal and the mechanical signal is received in the determined time interval. Therefore with this variant the unique measurable electrical signal is used to determine a prediction corridor, or confidence interval, for the expected mechanical signal.

If no mechanical signal has been received in the determined time interval or confidence interval, the time point of the heart movement can be set at a defined time point after the time point of the electrical excitation of the heart. This ensures that a trigger signal is sent out to the imaging facility anyway, even if no mechanical signal was received in the predetermined time interval. The defined time point after the time point of the electrical excitation of the heart can be determined beforehand based on empirical values.

The determination of the time point of the heart movement based on the mechanical signal can also be performed by extracting a feature from the mechanical signal, for example by first deriving and filtering the received mechanical signal.

This allows the components of the mechanical signal characterizing the event to be detected, specifically a defined heart movement, to be separated.

The receive time point can be determined as the time point after the first time point or in the determined time interval, in which the amplitude of the mechanical signal exceeds a predetermined threshold value.

In one embodiment of the method, the filtering of the mechanical signal can comprise filtering with a band pass filter. Alternatively the filtering of the mechanical signal can comprise filtering using a reference function. The reference function can comprise for example an M-wave or an M-signal. Convoluting the reference signal with the received signal does not allow the signal components associated with the M-signal to be filtered out in this instance. This embodiment is expedient when measuring the mechanical signal by way of a ballistocardiogram. The M-signal, also conventionally referred to as the M-wave of a ballistocardiogram, generally forms the feature of a ballistocardiogram that most reliably predicts the time point of a heart movement.

A pressure sensor can be used for example to acquire the mechanical signal. It allows a pressure wave triggered by the heart movement to be detected. This can be achieved for example by means of a sensor operating on the basis of the piezoelectric effect. Alternatively piezoresistive sensors can also be used for the pressure measurement. With these resistance elements are arranged on membranes, their resistance value being a function of the pressure acting on the membranes or the deformation of the membranes.

Capacitive pressure sensors can also be used. Capacitive pressure sensors can have for example two capacitor plates diffused into a silicon chip. A membrane is arranged between the capacitors or capacitor plates. When a pressure acts on the membrane, the distances between the membrane and the two opposing capacitor plates on both sides and thus the capacitances of the capacitors are changed in opposing directions. The capacitors are generally part of an internal amplifier, the output signal of which is a function of the difference in capacitances. Finally inductive sensors can also be used to measure the mechanical signal. The inductive pressure sensors can have for example an inductive path transducer, which is connected to a membrane.

When a pressure is applied to the membrane, the membrane moves. The movement of the membrane is transmitted to a movable iron armature, the position of which changes in opposing directions in two adjacent coils. The inductance therefore increases in one of the two coils, while it decreases in the other. The difference can be determined electrically in a very precise manner. Alternatively a differential transformer can also be used in the pressure sensors.

The EKG signal can be detected for example in a conventional surface measurement. With this the potential changes produced by the electrical excitation of the heart muscle cells brought about by the sinus node of the heart are derived by way of electrodes.

Alternatively the cited potential changes can also be measured using a capacitive sensor. The capacitive electrodes can derive the EKG signals for example contactlessly, in particular through the clothing of a patient.

The sensor is then completely electrically isolated from the patient. Active feedback is undertaken to keep the voltage constant.

The threshold value or reference value to be taken into account when measuring the mechanical signal can be determined as a function of an expected maximum amplitude of an M-signal. The values of the other maxima, for example of the K-wave or L-wave, can also be taken into account and the threshold value can be selected such that a trigger signal is only initiated when the M-signal occurs.

The evaluation facility can be set up to derive and filter the received mechanical signal. As already mentioned above, interference signals or signals that do not characterize the heart movement itself can be filtered out of the received mechanical signal or the signal characterizing the mechanical excitation of the heart by filtering.

The evaluation facility can also be set up to determine the receive time point of the mechanical signal as the time point after the first time point or in the determined time interval, in which the amplitude of the mechanical signal exceeds a predetermined threshold value. To determine the time point of the mechanical excitation of the heart, the time point at which a threshold value of the signal characterizing the mechanical excitation is exceeded is first determined. Combined with the information that the time point at which the threshold value is exceeded is located after the first time point or in the determined confidence interval, it is now possible to conclude with much greater certainty that the detected event is a signal with a fixed temporal relationship to the time point of the mechanical excitation of the heart, for example an M-signal of a ballistocardiogram. It is ultimately possible to conclude the time point of the mechanical excitation of the heart or of the movement of the heart from the determined time point of the signal with a fixed temporal relationship to the time point of the mechanical excitation of the heart and to use this information to control an image recording system in such a manner that image recording is for example not adversely affected by the heart movement.

FIG. 1 shows an example of a general schematic diagram of a computed tomography system, to clarify its general structure. The described method can also be applied to other imaging systems. However with a computed tomography system the most error-free recording possible is particularly important because of the necessity of keeping radiation exposure as low as possible, as repeated recordings are associated with additional radiation exposure for the patient. The arrangement comprises a gantry 2 with a stationary part 3 and with a part 4 that can be rotated about a system axis 5. The rotatable part 4 has a scan unit (x-ray system), which comprises an x-ray source 6 and an x-ray detector 7, which are arranged opposite one another on the rotatable part 4. During operation of the computed tomography system 1 x-ray radiation 8 travels from the x-ray source 6 in the direction of the x-ray detector 7, penetrates a measurement object P, for example a patient P, and is detected by the x-ray detector 7 in the form of measurement data or measurement signals.

FIG. 1 also shows a patient couch 9 for supporting a patient P. The patient couch 9 comprises a couch base 10, on which a support plate 11 provided to actually support the patient P is arranged. The patient support plate 11 can be moved relative to the couch base 10 in the direction of the system axis 5 so that it can be introduced, together with the patient P, into the opening 12 of the gantry 2 so that 2D x-ray projections of the patient P can be recorded. The computer processing of the 2D x-ray projections recorded using the scan unit or the reconstruction of slice images, 3D images or a 3D data record based on the measurement data or measurements signals of the 2D x-ray projections takes place using an image processor 13 of the computed tomography device 1, it being possible for the slice images or 3D images to be displayed on a display apparatus 14.

When the moving heart is being recorded, electrodes 20 and additional sensors (not shown) have to be positioned on the torso of the patient to be examined. The electrodes 20 and sensors are used to record information relating to the movement or time point of the movement of the heart. The recorded data is sent to an inventive heart movement determination apparatus 15.

The heart movement determination apparatus 15 comprises a first receive facility 16, which is set up to receive an EKG signal ES showing a heart movement. The heart movement determination apparatus 15 further comprises a timing facility 17, which is set up to determine for example a time interval I, in which a mechanical signal MS showing the heart movement will probably be received, as a function of the received EKG signal ES. The apparatus 15 also comprises a second receive facility 18. This receives a mechanical signal MS for example in the determined time interval I from sensors (not shown) positioned for example on the back of the patient. The apparatus 15 finally comprises an evaluation facility 19. The evaluation facility 19 determines the receive time point $T_2$ of the mechanical signal and a time point $T_3$ of a heart movement based on the determined receive time point $T_2$ of the mechanical signal.

Figure 2:
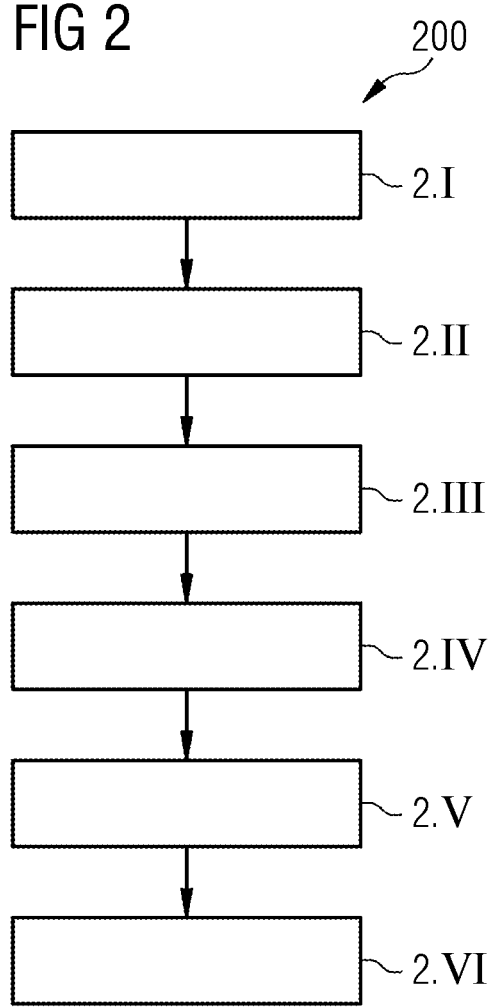
FIG. 2 shows a flow diagram illustrating a first example embodiment of the inventive method.

FIG. 2 illustrates the described method 200 in a flow diagram according to a first exemplary embodiment. In step 2.I an EKG signal showing a heart movement is received. In step 2.II a first time point $T_1$ is determined as a function of the received EKG signal, after which a mechanical signal showing the heart movement will probably be received. In step 2.III a mechanical signal is received after the determined first time point $T_1$. In step 2.IV the receive time point $T_2$ of the mechanical signal is determined. Then in step 2.V the time point $T_3$ of a heart movement is determined based on the determined receive time point $T_2$ of the mechanical signal. Finally in step 2.VI an initiation signal (trigger signal) is generated, which allows an imaging system to be synchronized with the heart movement.

Figure 3:
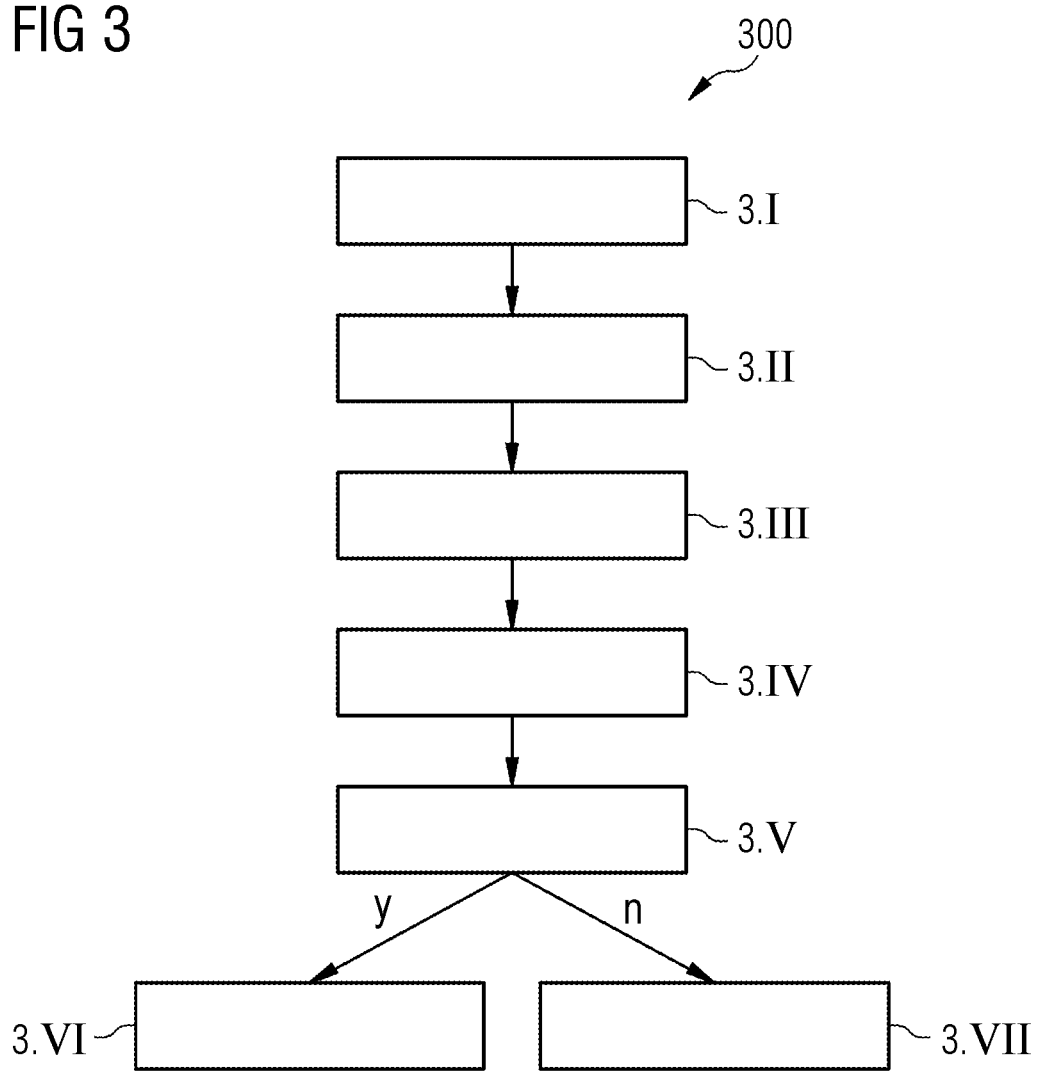
FIG. 3 shows a flow diagram illustrating a second example embodiment of the inventive method.

FIG. 3 shows a flow chart for a possible sequence according to a second exemplary embodiment of the inventive method 300. In a step 3.I an electrical signal, i.e. an EKG signal, is recorded and processed. In a step 3.II the electrical signal is used as a feature signal and the R-wave position for example is extracted in a prospective manner, in other words an internal trigger signal is generated with just a small offset in the region of a few milliseconds from a time point $T_0$, the receive time point of the EKG signal. In a step 3.III the internal trigger signal is used to determine or release an interval I, also referred to as a target corridor or confidence interval, for the mechanical signal, in which the mechanical signal or its feature signal will be received at a time point in a step 3.IV.

Figure 4:
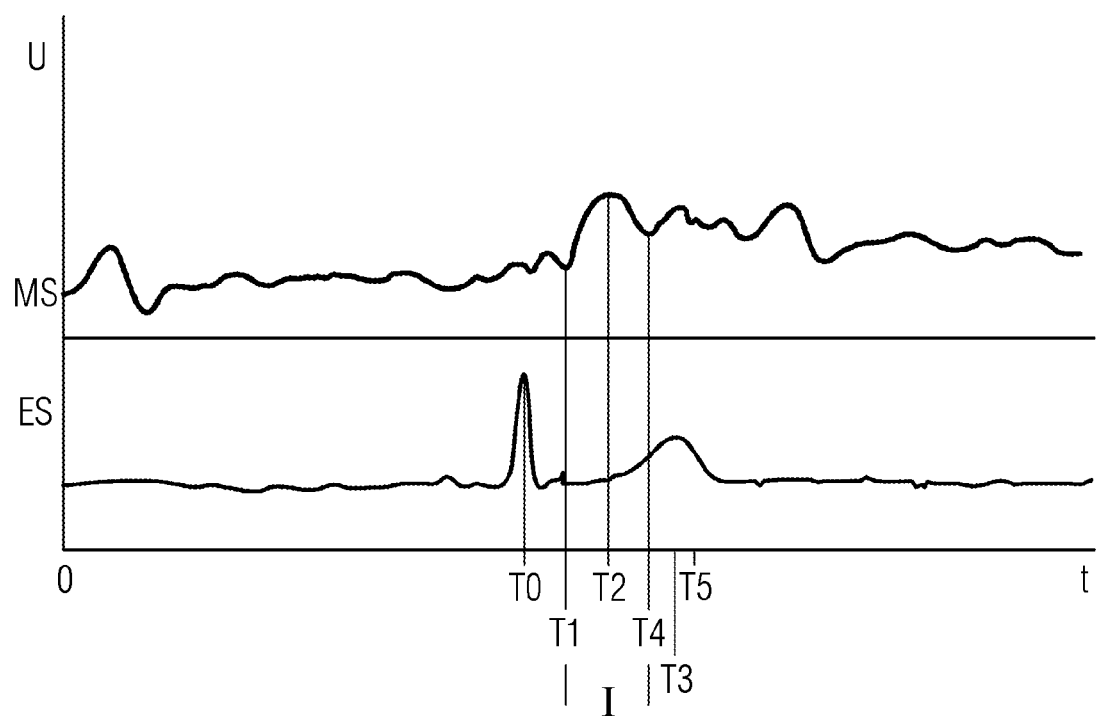
FIG. 4 shows a graph illustrating the time sequence of the method according to an example embodiment of the invention.

The interval I can start for example at a first time point $T_1$ and run until an end point $T_4$ (see FIG. 4). The received signal is compared in a step 3.V with a threshold value SW. If the threshold value is exceeded for example at a time point $T_2$, as shown by "y" in FIG. 3, in step 3.VI an initiation signal or trigger signal is output, which can be taken into account by an imaging system when recording images and characterizes a time point $T_3$ of a heart movement. If the threshold value is not exceeded in the entire interval I, i.e. before the end time point $T_4$ of the interval I, as shown in FIG. 3 by "n", in a step 3.VII for example an initiation signal can be output at a defined time point $T_5$ after the electrical excitation, in other words after the time point $T_0$.

This defined time point $T_5$ can be derived from the history of the offset between the electrical and mechanical excitation. In other words a statistically determined expected value for the offset between electrical and mechanical excitation can be known beforehand and is used in step 3.VII. Therefore if a confidence interval is determined instead of just a first time point $T_1$, after which the mechanical signal is expected, if no initiation signal is generated in the confidence interval, a replacement initiation signal can then simply be generated, which is transmitted at a determined time point.

The electrical signal can be generated for example by a conventional surface EKG. Alternatively capacitive sensors can also be used for example on the chest or back of the patient. The mechanical signal can be generated for example by a ballistocardiographic sensor. This can be done for example using a mat containing piezoelectrically active materials. Alternatively heart sounds can also be detected using a microphone. The S2 sound for example is used here. It is also possible to acquire the heart movement by means of an optically acquired signal using reflection pulse plethysmography. Finally it is also possible to use radar to measure either the movement of the body surface or a depth signal for heart movement.

FIG. 4 shows the time sequence of the method for determining the time point of a heart movement. Both an EKG signal ES and a mechanical signal MS are plotted one above the other. The time point $T_0$ of the excitation of the heart, characterized for example by a maximum of an EKG signal, in other words the R-wave, is also shown. The first time point $T_1$, at which the interval I starts, is also marked. The receive time point $T_2$ of the mechanical signal, at which the mechanical signal for example reaches its maximum or even exceeds a predefined threshold value SW, is also shown. The confidence interval I with the start time point $T_1$ and the end time point $T_4$, in which the mechanical signal MS is expected, is also shown. The determined time point $T_3$ of a heart movement detected as a function of the time point $T_2$ of the mechanical signal is also shown. Finally a time point $T_5$ is also shown, at which a trigger signal can be supplied as a replacement, if no mechanical signal MS has been received in the interval I.

Figure 5:
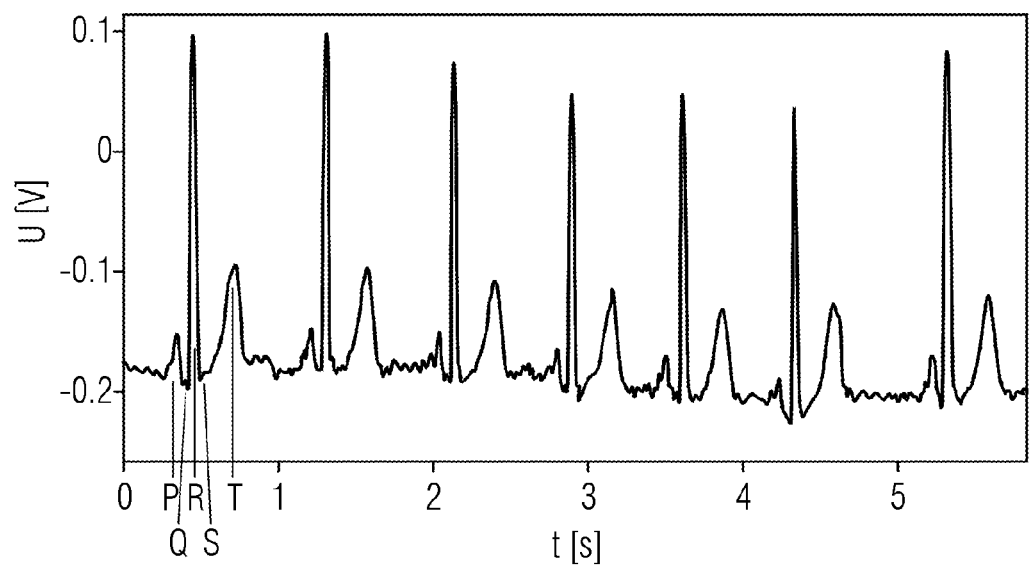
FIG. 5 shows a graph illustrating an electrocardiogram in a graphical manner.

FIG. 5 shows an EKG signal in a graphical manner. The EKG signal provides information relating to the electrical excitation of the heart muscle. The excitation usually originates from the sinus node. The excitation progresses to the other heart muscle cells from specialized heart muscle cells by way of the heart's electrical conduction system. These electrical voltage changes at the heart can be measured on the body surface and can be recorded over time, as shown in FIG. 5. A recurring image of electrical heart activity can be seen.

The surface EKG only shows the electrical activity of the heart muscle, not the actual mechanical heart movement or the actual ejection fraction of the heart as a function of time. The individual periodically recurring signal segments comprise a P-wave, a QRS complex, which corresponds to ventricular excitation, with a first negative deflection Q, a first very marked positive deflection R, also referred to as the R-wave, and a negative deflection S, which follows the R-wave. The signal segment also comprises a T-wave, which shows the repolarization of the ventricles and generally concludes the periodically recurring signal segment.

Finally the signal segment can also end with a U-wave, if for example subsequent fluctuations occur during ventricular repolarization, for example due to electrolyte imbalances. For signal emission the marked R-wave in particular is of interest and according to one exemplary embodiment it is also used as an internal initiation signal for determining an interval or target corridor for the mechanical signal.

Figure 6:
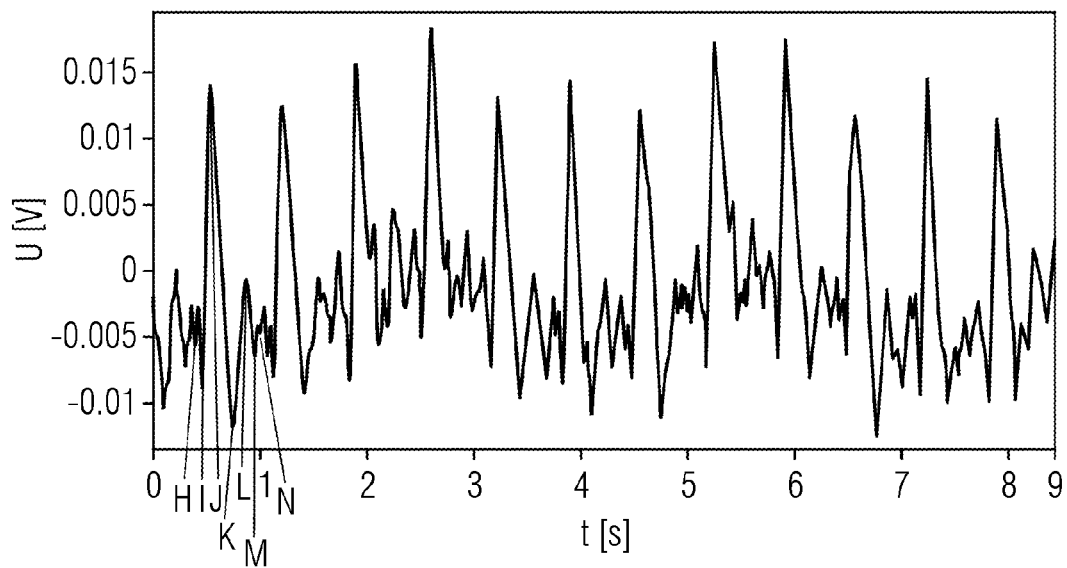
FIG. 6 shows a graph illustrating a ballistocardiogram in a graphical manner.

FIG. 6 shows the associated ballistographic signal (BKG), in other words a signal showing the mechanical heart movement. More precisely the ballistocardiogram registers oscillatory body movement produced by the mechanical activity of the heart and of the circulating blood. The waves that can be identified in the ballistocardiogram here result to some extent from the recoil associated with blood ejection, which is proportional to the quantity of blood and the acceleration imparted to the blood. However to some extent the waves are also due to the slowing of the blood flow speed in the aorta and to the impact of the blood against the curves of the aorta and the pulmonary artery as well as to the dividing and branching points of said vessels.

The ballistocardiogram also has characteristic waves. These are the systolic H-, I-, J- and K-waves as well as the diastolic L-, M- and N-waves. The first ventricular wave is the H-wave, which points in an upward direction and is produced by a body movement acting in a cranial direction. It starts around 0.02 s to 0.03 s after the start of the QRS complex in the electrocardiogram. The I-wave is produced by the recoil during the ventricular ejection period. The J-wave results from the impact of the blood ejected by the ventricles against the curves of the aorta and the pulmonary artery. In healthy people the J-wave is generally the dominant wave of the ballistocardiogram. The mean height of the I-wave is usually half that of the J-wave.

The K-wave is associated with the impact of the column of blood against the peripheral resistance of the vessels away from the heart. It is brought about by the slowing of the blood flow in the descending aorta and at the bifurcation of the abdominal aorta. The diastolic waves L, M and N occur as the heart relaxes and as the ventricles fill. However the graphical representations of a ballistocardiogram generally recorded are much more ambiguous than shown in FIG. 6 (see also FIG. 7).

Figure 7:
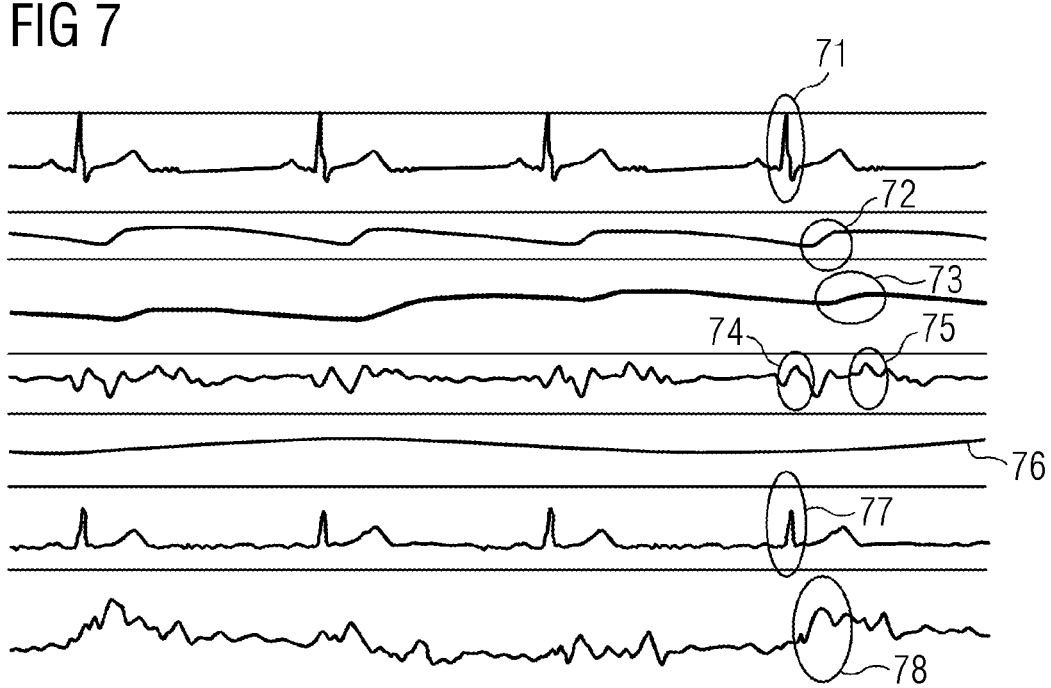
FIG. 7 shows a graph illustrating separated signals of a ballistocardiogram.

FIG. 7 shows a signal 71 of an electrocardiogram and for comparison a plurality of different signals based on mechanical measurements. The signal 72 is a reference PPG signal (PPG=photopletysmogram) of a pulse wave measured at a patient's ear. The signal 73 is a PPG on the back of a patient, which measures the pulse wave of the blood flowing through the back at the surface. The signal 74 is a PCG signal (PCG=phonocardiogram) on the back of the patient, which measures the sound particle velocity or more precisely the S1 sound. The signal 75 is also a PCG signal on the back of the patient, which measures the sound particle velocity or more precisely the S2 sound. The signal 76 is a reference respiration signal, which is measured for example using a pressure sensor. The signal 77 is a cECG signal (capacitive electrocardiogram) on the back of the patient, with the electrical excitation of the heart or more precisely the QRS complex or R-wave (encircled) being measured. The signal 78 is a BCG signal (BCG=BKG=ballistocardiogram), which measures the pressure velocity or the pressure at the surface of the back of the patient. The M-wave is encircled here.

If the BKG, as shown in FIG. 7, is now transformed into one or more feature signals, for example by derivation and filtering, either barely marked maxima can be seen, such as for example for the signals 72 and 73, or a number of maxima can be seen in the signal recording, as can be seen for example for the signals 74 and 75 as well as 78. The different successive maxima correspond to different signal components, for example the K- L- or M-wave of a signal characterizing the mechanical excitation of the heart, for example of a BKG.

The problem therefore arises that the individual signals associated with the corresponding heart movement or with a pressure change in the blood vessels around the heart cannot be separated completely even by filtering, for example using a reference signal, so that precise assignment of the maxima to a defined movement process of the heart is only possible with difficulty even after the mechanical signals have been filtered. If only a BKG signal were used as the basis for an initiation signal to activate or trigger an imaging system, there would be a large standard deviation for the offset or time interval between the maximum of the mechanical signal and the maximum of the electrical signal, as shown in FIG. 8.

Figure 8:
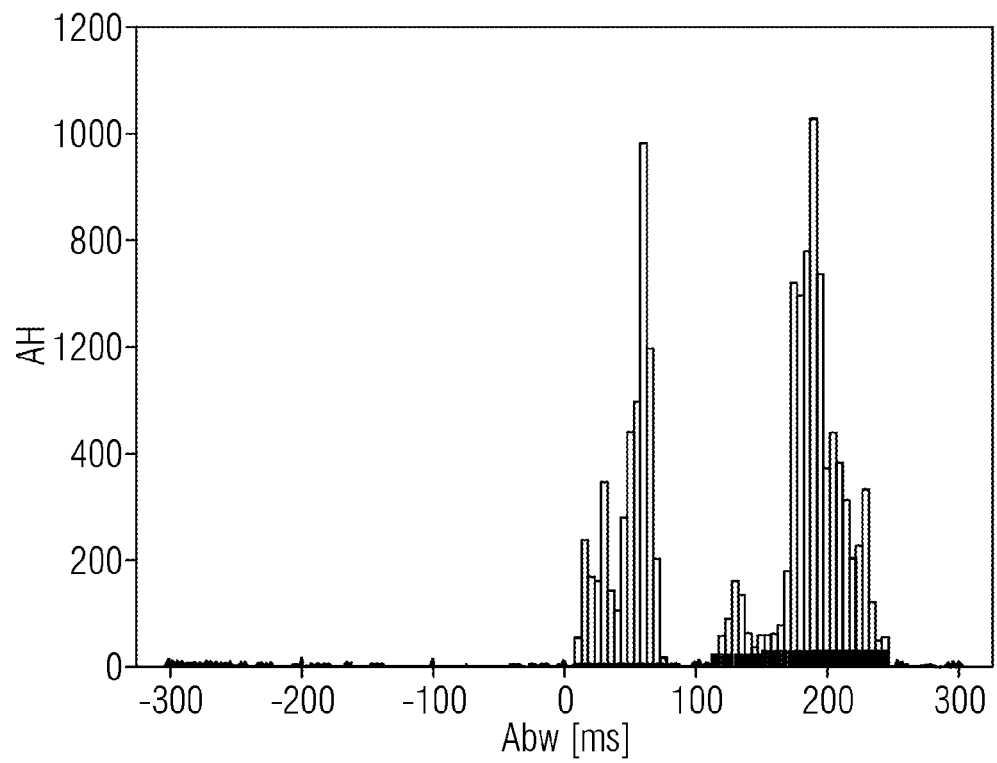
FIG. 8 shows a graph showing the deviation of the measured relative offset of the M-wave of the ballistocardiogram in relation to the R-wave of the electrocardiogram.

FIG. 8 shows the absolute frequency AH of the deviation of the offset over the deviation Abw from the reference in milliseconds. The occurrence of this deviation stems from the fact that during the acquisition of the signal characterizing the mechanical excitation of the heart the "correct" signal, for example the M-wave, is not always detected but in many instances an adjacent signal or the maximum of a temporally adjacent signal is also detected. This is frequently the case when the maxima of the temporally adjacent signals are very close to one another and also are either very barely marked or have at least a similar amplitude value. For this reason the R-wave of the EKG for example is used as an auxiliary signal, as the temporal relationship between the R-wave in the EKG and for example the M-wave in the BKG is known and constant within defined limits.

The auxiliary signal is used in such a manner that for example a time period, also referred to as a target corridor or confidence interval, is determined, in which the mechanical signal is expected. Thus maxima or more generally signal values, which are outside the target corridor, are excluded beforehand from the signal measurement of the mechanical signal and a certain minimum accuracy is also ensured when determining the time interval between the R-wave and the heart movement. This allows the BKG to be segmented using the information from the EKG. Determining the target corridor for the mechanical signal in any case prevents excessively large deviations of the mechanical signal due to other signal components of the mechanical signal. Thus a greater degree of accuracy is achieved when determining the time point of a heart movement compared with the simple use of a mechanical signal for the determination of the time point of the heart movement. As already mentioned above, instead of a target corridor it is possible just to determine a time point after which the mechanical signal is expected.

It should be noted that the features of all the exemplary embodiments or developments disclosed in the figures can be used in any combination.

It should finally be noted yet again that the method and structures described in detail above are exemplary embodiments and the basic principle can also be varied to a large degree by the person skilled in the art without departing from the scope of the invention, in so far as it is predetermined by the claims. Thus for example the apparatus 15, instead of being implemented separately, can also be configured as a component of the image processor 13 or additionally as a computer program running on the image processor 13. Similarly the apparatus 15 could also be implemented on a separate computation system, which is connected for example by way of a network to the imaging system 1. For the sake of completeness it should also be noted that the use of the indefinite article "a" or "an" does not exclude the possibility of the relevant features also being present in multiple form. Similarly the term "unit" does not exclude said unit consisting of a number of components, which can if necessary also be spatially distributed.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for determining a time point of a heart movement, the method comprising:
   receiving an EKG signal showing the heart movement;
   determining a first time point, after which a mechanical signal showing the heart movement is estimated to be received, as a function of the received EKG signal;
   receiving the mechanical signal after the first time point from a non-invasive sensor;
   determining a receive time point of the mechanical signal;
   determining the time point of the heart movement based on at least one of the determined receive time point of the mechanical signal and the first time point; and
   triggering an imaging system as a function of the determined time point of the heart movement.

2. The method of claim 1, further comprising:
   determining a second time point as a function of the received EKG signal, a time interval being between the first time point and the second time point, the time interval representing an interval in which the mechanical signal showing the heart movement is estimated to be received.

3. The method of claim 2, wherein if no mechanical signal has been received in the time interval, the determined time point of the heart movement is set at a defined time point after a time point of an electrical excitation of the heart, the time point of the electrical excitation of the heart being indicated in the EKG signal.

4. The method of claim 1, wherein the receiving the mechanical signal includes deriving and filtering the mechanical signal.

5. The method of claim 1, wherein the determining the receive time point determines the receive time point as a time point in which an amplitude of the mechanical signal exceeds a threshold value.

6. The method of claim 1, wherein the non-invasive sensor is a pressure sensor.

7. The method of claim 1, wherein the receiving the EKG signal receives the EKG signal using a capacitive sensor.

8. The method of claim 5, wherein the threshold value is based on a function of an expected maximum amplitude of an M-signal.

9. An apparatus for determining a time point of a heart movement, comprising:
   a first receive facility, to receive an EKG signal characterizing the heart movement;
   a timing facility, to determine a first time point, after which a mechanical signal showing the heart movement is estimated to be received, as a function of the received EKG signal;
   a second receive facility, to receive the mechanical signal after the first time point from a non-invasive sensor; and
   an evaluation facility, to determine a receive time point of the mechanical signal and to determine the time point of the heart movement based on at least one of the determined receive time point of the mechanical signal and the first time point and to trigger an imaging system as a function of the determined time point of the heart movement.

10. The apparatus of claim 9, wherein the timing facility is configured to determine
   a second time point as a function of the received EKG signal, a time interval being between the first time point and the second time point, the time interval representing an interval in which the mechanical signal showing the heart movement is estimated to be received.

11. The apparatus of claim 9, wherein the evaluation facility is configured to derive and filter the received mechanical signal.

12. The apparatus of claim 9, wherein the evaluation facility is configured to determine the receive time point as a time point at which an amplitude of the mechanical signal exceeds a threshold value.

13. A non-transitory computer-readable medium storing instructions, when executed by a processor, configured to cause the processor to execute the method of claim 1.

14. The method of claim 2, wherein the receiving the mechanical signal includes deriving and filtering the mechanical signal.

15. The method of claim 3, wherein the receiving the mechanical signal includes deriving and filtering the mechanical signal.

16. The apparatus of claim 10, wherein the evaluation facility is configured to derive and filter the received mechanical signal.

17. The apparatus of claim 10, wherein the evaluation facility is configured to determine the receive time point as a time point at which an amplitude of the mechanical signal exceeds a threshold value.

* * * * *